United States Patent [19]

Bauermeister

[11] 4,248,712
[45] Feb. 3, 1981

[54] ELECTRODE DEVICE

[75] Inventor: Gerd D. Bauermeister, Isernhagen, Fed. Rep. of Germany

[73] Assignee: Gesellschaft fur Biotechnologische Forschung mbH, Braunschweig-Stockheim, Fed. Rep. of Germany

[21] Appl. No.: 1,458

[22] Filed: Jan. 8, 1979

[30] Foreign Application Priority Data

Jan. 12, 1978 [DE] Fed. Rep. of Germany ....... 2801223

[51] Int. Cl.³ .......................................... G01N 27/30
[52] U.S. Cl. ................................. 204/195 P; 128/635
[58] Field of Search ........... 204/195 P, 195 M, 195 B; 128/635; 324/29

[56] References Cited
U.S. PATENT DOCUMENTS

| 3,503,861 | 3/1970 | Volpe | 204/195 P |
| 3,577,332 | 5/1971 | Porter et al. | 204/195 P |
| 3,718,562 | 2/1973 | Haddad | 204/195 P |
| 3,826,730 | 7/1974 | Watanabe et al. | 204/195 P |

FOREIGN PATENT DOCUMENTS

| 2124445 | 11/1971 | Fed. Rep. of Germany . | |
| 1598397 | 9/1974 | Fed. Rep. of Germany . | |
| 2410809 | 9/1975 | Fed. Rep. of Germany | 324/29 |
| 1033171 | 6/1966 | United Kingdom . | |
| 1166683 | 10/1969 | United Kingdom | 204/195 P |

*Primary Examiner*—G. L. Kaplan
*Attorney, Agent, or Firm*—Hammond & Littell, Weissenberger and Muserlian

[57] ABSTRACT

An electrode device having an electrolyte container separated from the test medium by a membrane member, a cathode within the electrolyte container having the shape of the end section of a precious metal conductor protruding from an insulating body and a reference electrode being provided within the electrolyte container characterized in that the electrolyte container is sealed as a pressure chamber during sterilization whereby the pressure on each side of the membrane member remains substantially the same during sterilization.

4 Claims, 7 Drawing Figures

ELECTRODE DEVICE

The German Pat. No. 1 598 397 states that measuring head and electrolyte must not be subjected to hot steam during a hot steam sterilisation since this would destroy the electrode or at least change the calibration curve of the electrode. Therefore, a robust membrane having a thickness in the range of 50 to 1,000 microns is suggested so that the insertion, carrying the electrode, can be removed and inserted, respectively, without any destruction of the membrane. However, such an inserting and removing, respectively, is detrimental with respect to the time consumed.

In addition, in G-I-T (Fachzeitschrift für das Laboratorium) 20 (1976) 977 to 984 it is disclosed on page 983 left that thin membranes are advantageous; thicknesses in the range of 10 to 25 microns are mentioned. As an example of an electrode having an obviously thin membrane, the so-called IL-Electrode is mentioned which is described in the German Pat. No. 2 124 445 and U.S. Pat. No. 3,718,562. Such thin membranes, however, do not endure great pressure differences as can be inferred from the German Pat. No. 1 598 397 and G-I-T loc. cit. page 983 left. Therefore, it is not possible to sterilise an IL-Electrode in such a manner that during the sterilisation pressure is applied onto the thin membrane only from the side of the test medium. This would be the case if, for example, the electrolyte container with the thin membrane and without any insertion were installed in a fermenting reactor which was be heated up to a sterilization temperature of 120 degrees C. Neither is it possible to sterilise an IL-electrode in a satisfying manner so that pressure is applied to both sides of the membrane. Since the installed cathode biases the thin membrane, the membrane would be irreversibly deformed during sterilisation as can be indirectly drawn from G-I-T loc. cit. page 983 left.

According to the British Pat. No. 1,033,171 it is possible to apply pressure on the rod 6 carrying the cathode by screwing the screw 13 down. This known prior art, however, does not deal with the problem of sterilisation. Therefore, it is not surprising that this patent does not give any detailed comments on how the electrolyte can be filled into the electrolyte container. If the filling is carried out through a nozzle not shown, it is possible to assume that this nozzle cannot be closed to take up that part of the electrolyte which is displaced when the screw 13 is screwed down. Therefore, the stress applied to the membrane member of this known electrode device cannot be relieved when a sterilization is carried out. Therefore, it is an object of the invention to provide an electrode device which is ready for use practically immediately after sterilization, and which can be used once again after taking only a few measures. This electrode device is designed to be used (inter alia) for the same purposes as the electrodes of the prior art mentioned above.

The following requirements must be met to solve the said problem:

It should be possible to sterilize the electrode device after it has been put together and installed;

the membrane should be relieved during a sterilisation;

the pressure applied by the cathode to the membrane before and after the sterilisation should be the same;

it should be possible to fill the electrode device with an electrolyte before or after a sterilisation without disassembling it;

the electrode device should have a short starting time;

the electrode device should have a long lifetime;

the reference electrode should have a constant resistivity;

it should be possible to exchange the reference electrode rapidly, if necessary;

in addition, it should be possible to rapidly exchange the membrane in contact with the cathode, if necessary;

finally, it should be possible to stretch this membrane evenly and symmetrically, respectively.

Of course, solving one or several of the said partial problems would offer benefits.

The problem from which the invention starts is solved by an electrode device which comprises an electrolyte container, the opening of the electrolyte container towards the test medium being closed by a membrane member, a cathode being disposed in the electrolyte container and having the shape of the end section of a precious metal conductor protruding from an insulating body, and a reference electrode being disposed in the said electrolyte container, the said electrode device being characterized in that the electrolyte container forms a pressure chamber which relieves the membrane member of any stress applied during the sterilisation. For this reason the electrode device can be sterilized even when it is put together and inserted.

Since the insulating body with the cathode is displaceable perpendicularly with respect to the plane of the membrane member in a manner known per se the membrane member can be relieved of the stress due to cathode pressure during the sterilisation so that an irreversible deformation is not possible. Since, in addition, the insulating body with the cathode, when lowered, is biased by a spring against the membrane member a reproducible pressure of the cathode surface on the membrane member can be achieved when the electrode device is used. In addition, a possible slight inward deformation of the membrane member can be compensated for.

The membrane member can cover the opening of the electrolyte container from inside the electrolyte container in a manner known per se, the opening being tapered towards the test medium. The membrane member is supported by this conical opening so that a very small free membrane surface can be provided, and, for example, a thin supporting membrane and/or a thin inner membrane can be used; this reduces the start-up time considerably. The smallest diameter of a circular opening can be in the range of from three to five mm and especially about 4 mm.

When the electrolyte container comprises a sleeve and a sleeve cap having an opening towards the test medium, the sleeve of the electrolyte container can be provided with an outer circumferential shoulder for the insertion of a sealing membrane stretching ring at the end of the sleeve which is directed towards the sleeve cap, the membrane stretching ring protruding somewhat over the face of the sleeve when the sleeve cap is not pressed against the sleeve. In addition, a clearance is provided for the outwardly directed expansion of the membrane stretching ring in the plane of both membranes. If the sleeve is pressed against the sleeve cap the membrane stretching ring can radially and outwardly escape only along the plane of the inner membrane whereby the inner membrane is stretched evenly and symmetrically, respectively. This embodiment makes the use of O-rings which sit on the sleeve cap dispensable. In addition, these do not guarantee an even stretching of the membrane.

It is advantageous if the outer diameter of the inner membrane (in case the membrane member comprises an inner membrane and the supporting membrane) and the outer diameter of the membrane element, respectively, correspond approximately to the outer diameter of the membrane stretching ring. In addition, the membrane stretching ring and the membrane member and the inner membrane, respectively, can be fixedly combined with each other or form an integral element.

Conveniently, the supporting membrane is stuck on to the inner side of the sleeve cap; in this case the inner membrane is not combined with the supporting membrane so that the inner membrane can slide on the supporting membrane.

The electrode device is provided with pressure resistant valves for the introduction or removal of the electrolyte, the inlet and outlet, respectively, of the electrode device being in connection with the electrolyte container. In this case, the electrolyte container can be filled with the electrolyte before or immediately after a sterilisation. In either event, it is not necessary to take the electrode device apart.

The end of the reference electrode which does not dip into the electrolyte can form one part of a plug connection, so that the reference electrode can easily be exchanged or cleaned.

If the reference electrode enters the electrolyte container through a flexible sealing the electrolyte cannot penetrate between the reference electrode, the electrolyte container, and the sealing, so that the resistivity characteristics of the reference electrode can be maintained.

If the end section of the reference electrode which dips into the electrolyte is formed like a crown or a spiral or a ball of wire, a fairly large electrode surface is provided.

The following description will explain the invention in greater detail with reference to figures.

Figure 1:
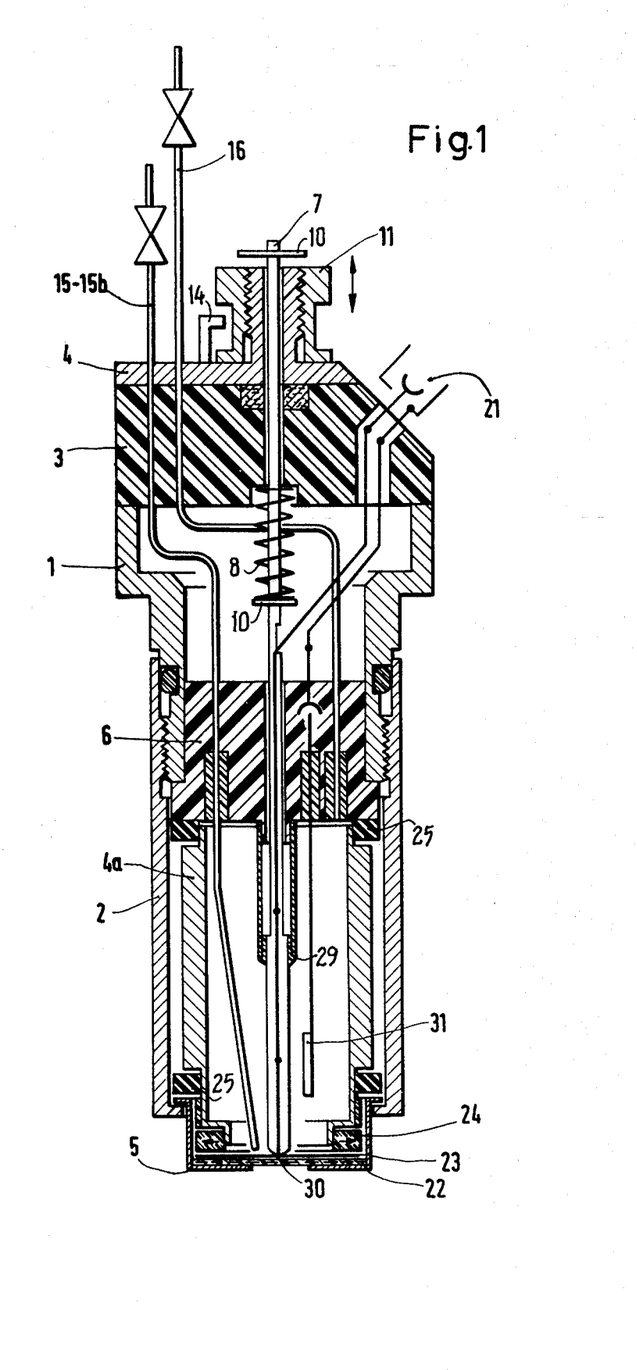
FIG. 1 shows a general sectional view of the electrode device according to the invention.

FIG. 1 shows a cylindrical housing 1 carrying a housing head 3 and a housing cover 4 on its upper side and a housing cap 2 with a sleeve cap 5 on its lower side. The sleeve cap 5, the electrolyte chamber sleeve 4a and the electrolyte chamber block 6 form the electrolyte chamber. A filling pipe 15, 15b and a ventilating pipe 16 are equipped with valves and passed through the housing cover 4 and the electrolyte chamber block 6 and are connected with the electrolyte chamber. The inner membrane 23 disposed on the inner side of the sleeve cap 5 is supported by the supporting membrane 22 and can be stretched by the isolating and stretching sealing ring 24 when the housing 1 and the housing cap 2 are screwed together. The cathode carrier 7 is pressed by a spring 8 against the membranes 22, 23 and can be lifted a present distance by turning the nut 11. The lead wires for the cathode 30 and the anode 31 start from the plug and socket 21, respectively.

There follows a detailed description of the electrode device according to the invention of FIGS. 2–7. This electrode device comprises a cylindrical housing 1, a cylindrical housing cap 2, a housing head 3, and a housing cover 4. The housing 1, the housing cap 2, and the housing cover 4 can, for example, consist of stainless steel and the block-like housing head can, for example, consist of an isolating synthetic material like Delrine.

The housing 1 has been inserted into the electrolyte chamber block 6 which consists for example of an insulating synthetic material like Araldite. This electrolyte chamber block 6 is provided with a circumferential shoulder which abuts against the lower face of the housing 1.

The upper final section of the housing cap 2 has been screwed on to the lower final section of the housing 1, the upper end section of the housing cap 2 covering an outer circumferential groove of the housing 1 which houses the sealing O-ring 27 made of, for example, Ethylene/Propylene. For example, the housing cap 2 can be screwed on to the housing 1 to such an extent that it abuts against an outer circumferential protrusion of the housing 1.

The lower end of the housing cap 2 is provided with an inner circumferential protrusion. A sleeve cap 5 has been inserted into the opening (formed by the protrusion) in a telescope-like manner; the sleeve cap 5 can be made of, for example, stainless steel. This sleeve cap 5 is provided with an outer circumferential protrusion at the upper end of the sleeve cap 5 the protrusion being supported by the protrusion of the housing cap 2. The disc-like face of the sleeve cap 5 is provided with a centric circular opening having a conical shape. The smallest diameter of this opening is about 4 mm, but can be smaller or greater, e.g., 3 to 5 mm. The disc-like face of the sleeve cap 5 supports a supporting membrane 22 inside, which can be, for example, a stainless steel net covered with a silicone resin. This supporting membrane 22 can be stuck on to the sleeve cap 5. The supporting membrane 22 supports an inner membrane 23 in loose contact which, for example, can be made of Polytetraflour ethylene (Teflon).

A cylindrical sleeve (electrolyte chamber sleeve) 4a can be inserted into the unit formed by the housing cap 2 and the sleeve cap 5; the sleeve 4a can be made of, for example, steel. This sleeve 4a has such an outer diameter that the sleeve 4a does not abut against both the housing cap 2 and the cylindrical section of the sleeve cap 5. The isolating sealing rings 24, 25, 25 and 32 insulate the sleeve 4a against the unit formed by the housing cap 2 and the sleeve cap 5; in addition, they guarantee that the electrolyte does not penetrate into the ring gap formed by the sleeve 4a on the one hand and the housing cap 2 and sleeve cap 5 on the other hand. The insulating sealing rings 24, 25, 25 and 32 can be made of, for example, a silicone resin or a Polytetraflour ethylene.

When the housing cap 2 is screwed onto the housing 1, the electrolyte chamber block 6 is pressed against the upper insulating sealing ring 25. This pressure is transferred by the sleeve 4a to the insulating sealing ring 24. The upper and inner side of this isolating sealing ring 24 abut against a shoulder which is provided at the outer periphery of the lower end section of the sleeve 4a. By this construction sealing ring 24 on stretching cannot escape inwardly when being compressed. Since, however, the stretching sealing ring 24 has enough clearance with respect to the sleeve cap 5 it can expand with the pressure radially outwards. By this expansion movement the inner membrane 23 is stretched evenly and symmetrically, respectively.

The housing cover 4, the housing head 3 and the electrolyte chamber block 6 are provided with a central bore hole through which a displaceable cathode carrier 7 is passed which can be made of, for example, stainless steel. The lower end section of the cathode carrier 7 is provided with a broadened cylindrical section into which a glass tube has been inserted by means of a tube-like sealing 29 which can be, for example, a silicone tube. This glass tube contains a wire of precious metal (e.g., a platinum wire) as cathode; the glass tube is sealed by melting on its lower end and the cathode protrudes from the middle and the top, respectively, of the melting area. The upper end of the wire of precious metal is welded on a copper wire in the glass tube and a lead wire is soldered on to the copper wire.

A socket 21 has been screwed into the housing head 3 until abutting on the spacer 20 which can be made of, for example, Delrine. A lead wire, starting from the socket, 21 passes through a bore hole in the housing head 3 and enters a chamber formed by the housing head 3, the housing 1, and the electrolyte chamber block 6, and in this chamber enters the cathode carrier pipe 7 where the lead wire is soldered on to a copper wire.

The cathode carrier pipe 7 is provided with a Seeger ring 10 in the chamber formed by the housing head 3, the housing 1 and the electrolyte chamber block 6; the Seeger ring 10 supports a socket 9. This socket 9 and the housing head 3 serve as an abutment for a spiral spring 8 which surrounds the cathode carrier pipe 7. The Seeger ring 10, the spring socket 9 and the pressure spring 8 can be made of, for example, stainless steel. This spring 8 through its action on the cathode carrier pipe acts to stretch the membrane 23 evenly and symmetrically, respectively.

The housing cover 4 is provided with a central nozzle directed upwardly and a central nozzle directed downwardly through which the cathode carrier pipe 7 is passed in a displaceable manner. The lower nozzle is fitted into a corresponding hollow of the housing head 3 where the sealing ring 19 is disposed, which can be made of, for example, felt. The upper nozzle is provided with an outer thread on to which a nut 11 is screwed. The upper face of this nut 11 supports a washer 13. The nut 11 and the washer 13 can be made of, for example, stainless steel. The end of the cathode carrier pipe 7 passes the washer 13 and is provided with a Seeger ring 10 which serves as an abutment for the washer 13. When the nut 11 is screwed in the direction opposite to the housing cover 4 the washer 13 abuts against the Seeger ring 10 so that the cathode carrier pipe 7 is lifted and the cathode 30 is separated from the membrane 23. The nut 11 (and thereby the cathode carrier pipe 7) are covered by a cap 12 made of, for example, Delrine. The lower end of the nut 11 is provided with an outer circumferential protrusion which engages with a stop and abutment 14, respectively, made of, for example, stainless steel when the cathode 30 is sufficiently separated from the membrane 23. As has been already mentioned a bore hole leads from the socket 21 which is displaced in the housing head 3 to the chamber which is formed by the housing head 3, the housing 1 and the electrolyte chamber block 6. In addition to the lead wire for the cathode a lead wire for the anode starts from this socket, which also passes the bore hole and the chamber and ends in a socket 33a (and a plug 33, respectively) which is provided in or at the electrolyte chamber block 6 and is fixed in the electrolyte chamber block 6 by, for example, a safety pin 34 e.g., a stainless steel wire. The reference electrode and anode 31, respectively, made of, for example, silver is put into this plug 33. This reference electrode 31 passes a bore hole in the electrolyte chamber block 6 and enters the electrolyte chamber through an insulating sealing 26, e.g., a silicone tube. This sealing 26 seals the said bore hole of the electrolyte chamber block 6 and guarantees that the socket 33 comes into contact with the electrolyte only through the anode 31. In addition, the said sealing 26 guarantees the constant resistivity of the reference electrode 31. The reference electrode 31 can be a wire which is bent in the shape of a crown in the neighbourhood of the cathode 30.

Figure 2:
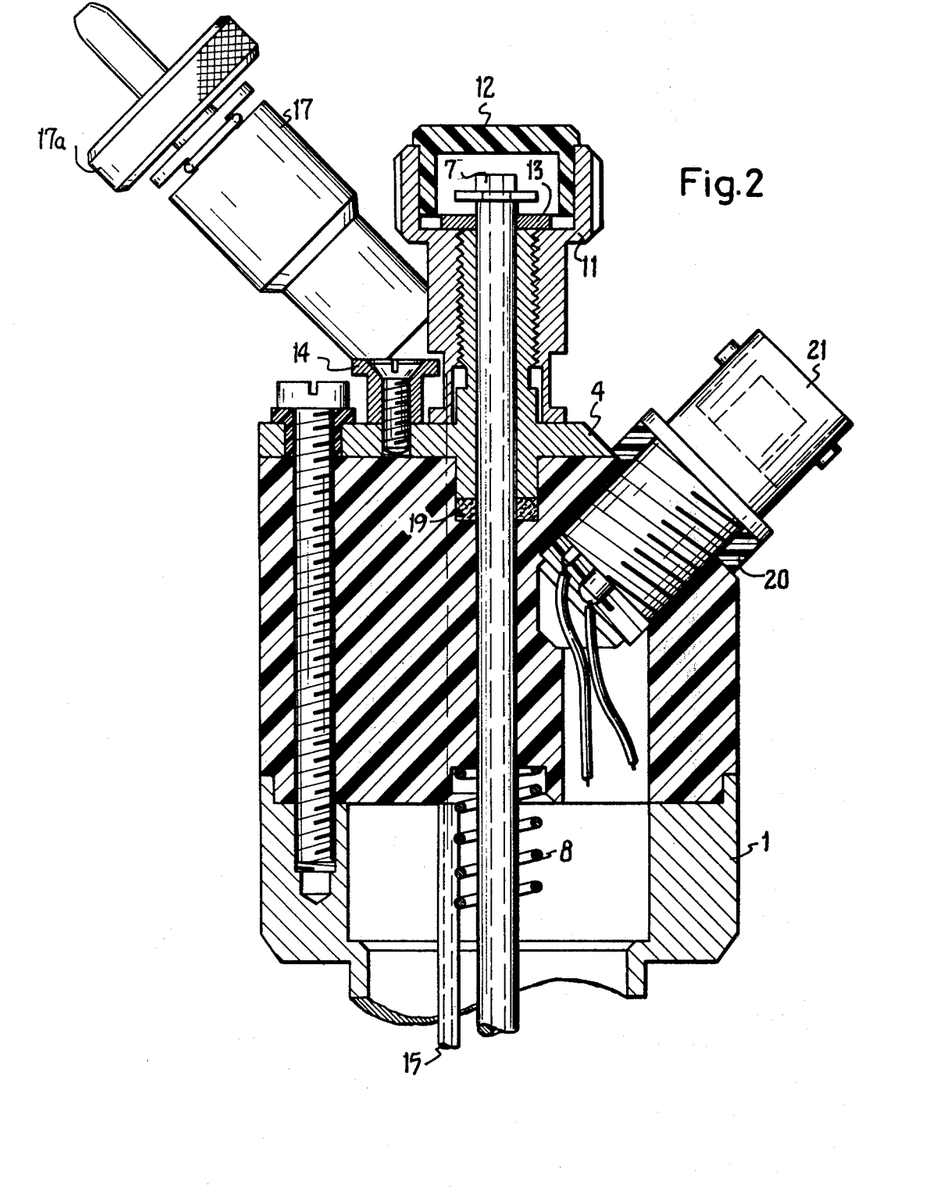
FIG. 2 shows a partial sectional view (section C–D in FIG. 4) of the upper part of an electrode device according to the invention, the lower part of the electrode device being removed.
Figure 3:
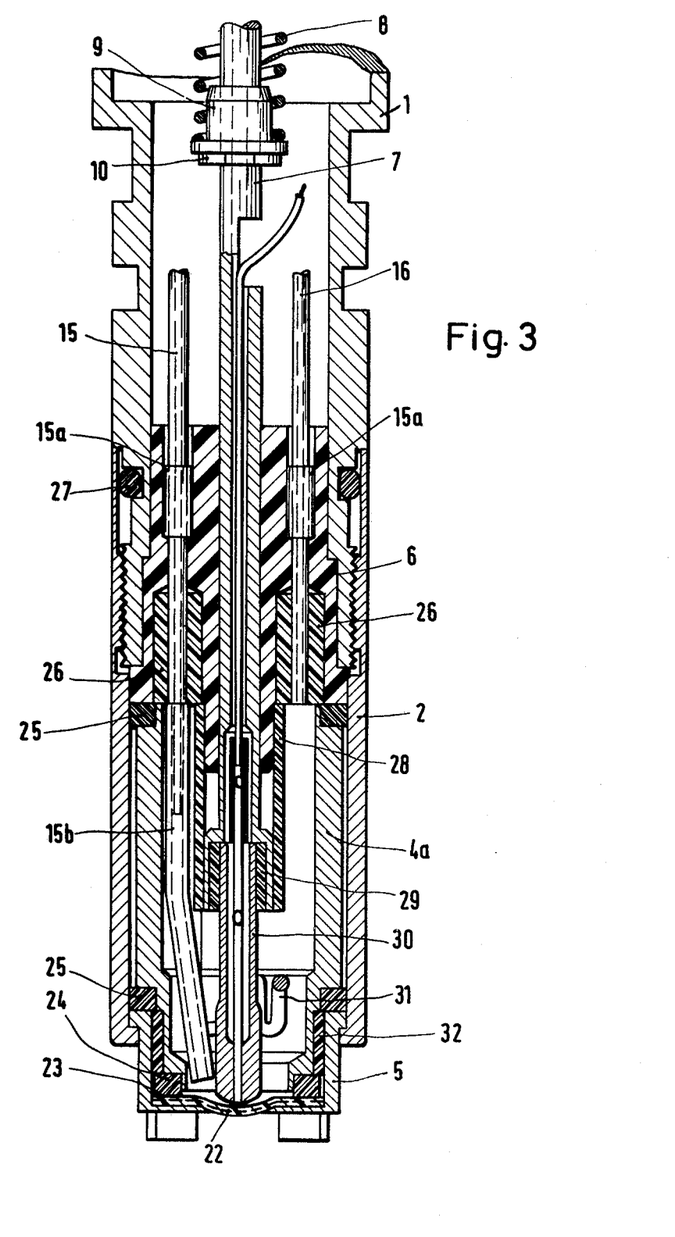
FIG. 3 shows a partial sectional view (section A–B in FIG. 4) of the electrode device according to FIG. 1 the upper part of the electrode device being removed.
Figure 4:
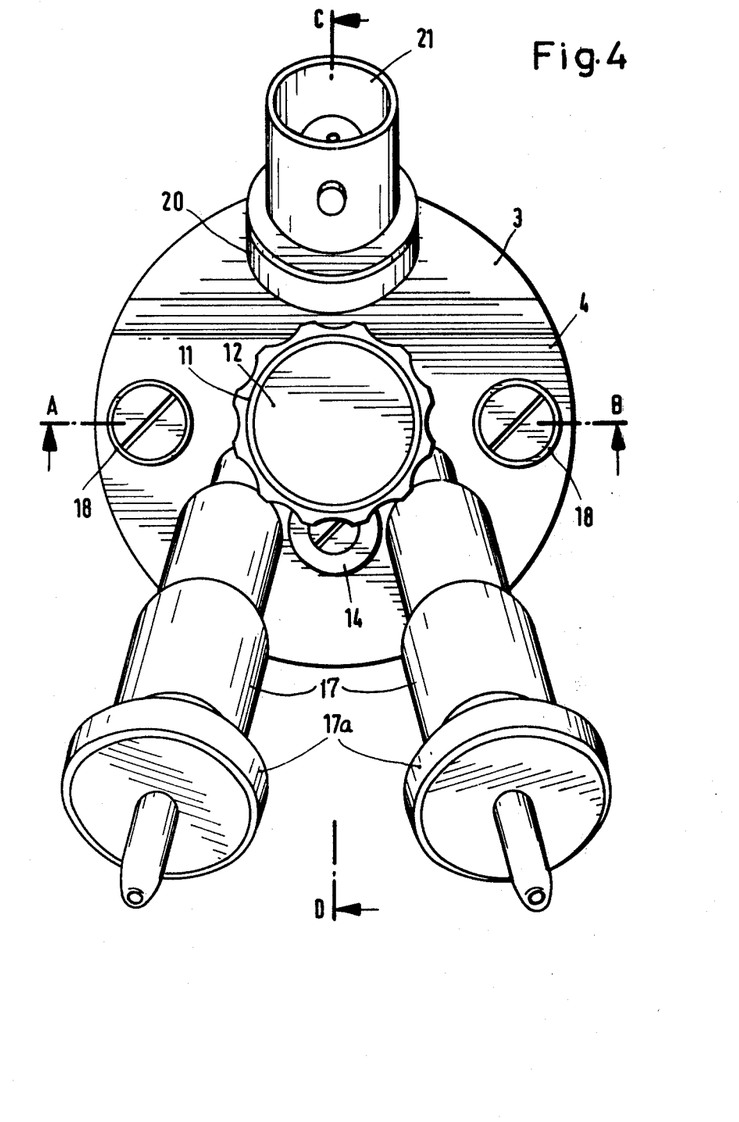
FIG. 4 shows a plane view of the electrode device according to FIGS. 2–3.
Figure 5:
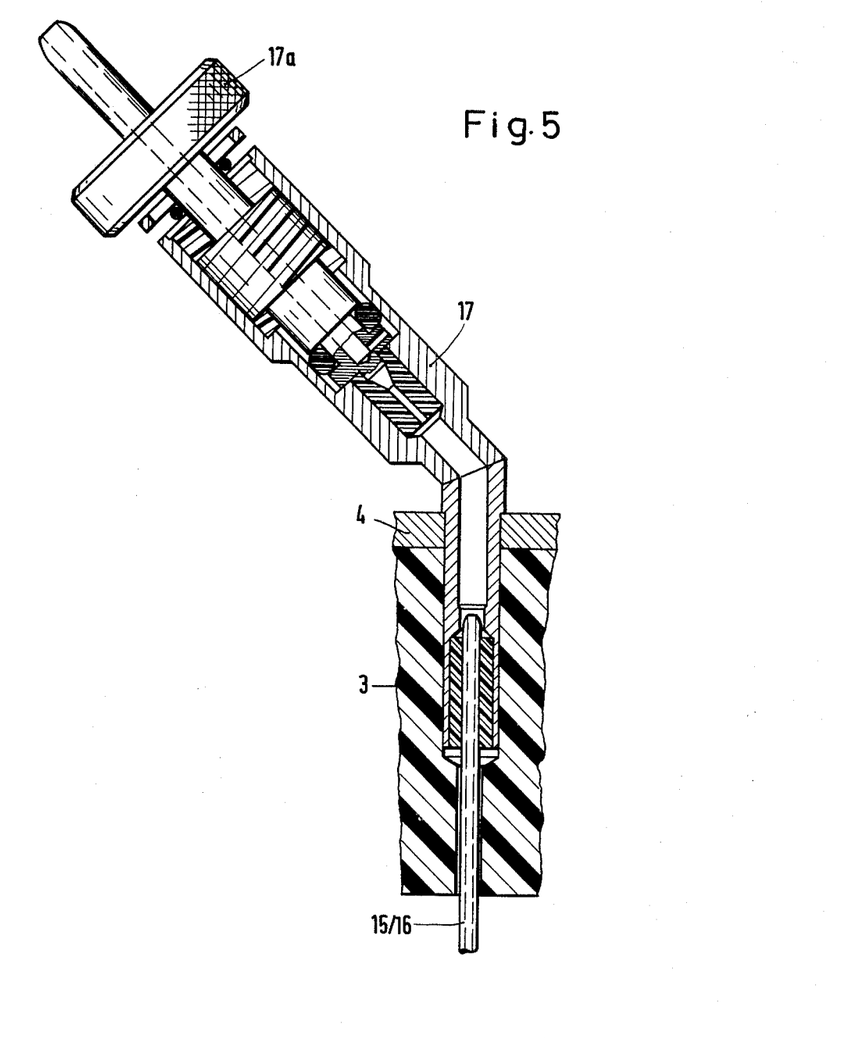
FIG. 5 shows a partial sectional view of a valve according to FIGS. 2 and 4.
Figure 6:
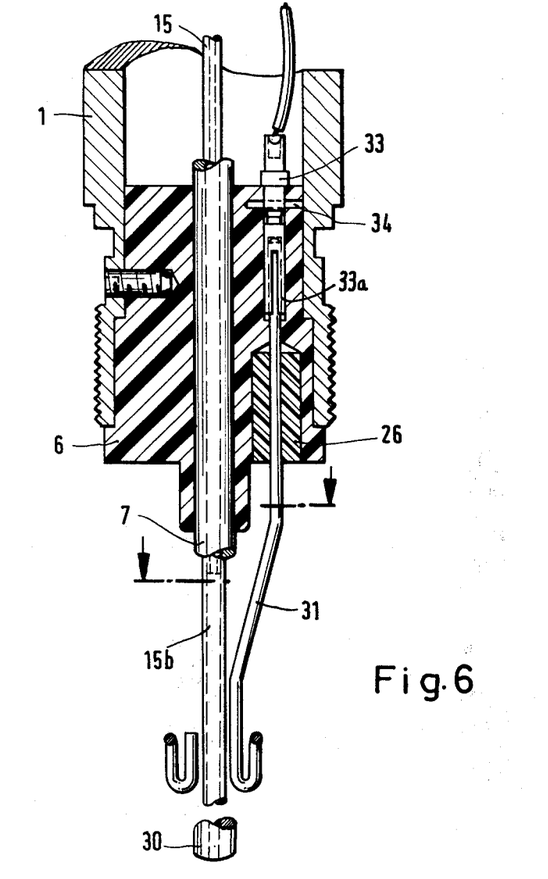
FIG. 6 shows a partial sectional view (C–D in FIG. 4) of the middle section of the electrode device according to FIGS. 2 to 5, the upper section and the lower section of the electrode device being removed.
Figure 7:
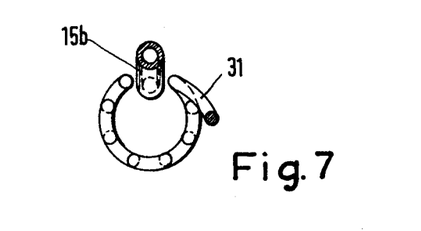
FIG. 7 shows a plane view of the lower section of the reference electrode and the electrolyte inlet.

Two valves strong enough to resist the pressure caused by sterilisation are provided on the housing cover 4, which comprise a valve housing 17 and a valve spindle 17a in a usual manner and which can be made of, for example, stainless steel. Rotation of the spindles 17a closes or opens both the filling pipe 15 and the ventilating pipe 16. When the valves are 17 closed pressure build-up caused by sterilisation in the electrolyte chamber is contained in said chamber. The filling pipe 15 starting from a valve passes a bore hole of the housing head 3, the chamber formed by the housing head 3, the housing 1 and the electrolyte chamber block 6, and finally a bore hole of the electrolyte chamber block 6 and enters the electrolyte chamber. The bore hole leading through the electrolyte chamber block 6 comprises three successive cylindrical sections, the middle section being the narrowest one and the lower section the broadest one. The upper cylindrical bore hole section forms a place for a fitting pipe and fitting sleeve 15a, respectively, which is fixed on the filling pipe 15; the filling pipe 15 and the fitting pipe 15a can be made of, for example, stainless steel. A sealing 26 (e.g., a silicone tube) is fitted into the lower cylindrical bore hole section and the filling pipe 15 enters the electrolyte chamber through this sealing 26. A tube 15b (made of, for example, Polytetrafluor ethylene) is pulled over the end of the filling pipe 15 disposed in the electrolyte chamber; the tube 15b extends near to the membrane 23.

The above description of the valve and the filling pipe 15 applies in a corresponding manner to the other valves with the exception that a ventilating pipe 16 (made of, for example, stainless steel) corresponds to the filling pipe and that the end of this ventilating pipe 16 is disposed at the highest level of the electrolyte chamber.

Delrine = acetalhomopolymer of formaldehyde having a form stability at more than 120 degrees C.

I claim:

1. Electrode device having an electrolyte container, the opening towards the test medium being closed by a membrane member, a cathode being provided within the electrolyte container and having the shape of the end section of a precious metal conductor protruding from an insulating body, the insulating body being displaceable perpendicularly with respect to the plane of the membrane element, and a reference electrode being provided within the electrolyte container, further characterized in that the electrolyte container is a pressure chamber equipped with pressure resistant valves for introducing and removing an electrolyte and that the insulating body is biased by a spring against the membrane member and can be separated from the membrane member during a sterilization.

2. Electrode device according to claim 1 further characterized in that the electrolyte container comprises a sleeve and a sleeve cap having an opening towards the test medium and that the end of the sleeve in the direction of the sleeve cap is provided with an outer circumferential shoulder for inserting a sealing membrane stretching ring, the membrane stretching ring protruding somewhat over the face of the sleeve when the sleeve is not pressed against the sleeve cap and an outer clearance surrounding the membrane stretching ring being provided for the expansion of the membrane stretching ring directed outwardly in the plane of the membrane member.

3. Electrode device according to claim 2, further characterized in that the outer diameter of the membrane member corresponds approximately to the outer diameter of the membrane stretching ring.

4. Electrode device according to claim 3, further characterized in that a supporting membrane is attached to the inner side of the sleeve cap.

* * * * *

UNITED STATES PATENT AND TRADEMARK OFFICE
CERTIFICATE OF CORRECTION

PATENT NO. : 4,248,712
DATED : February 3, 1981
INVENTOR(S) : GERD D. BAUERMEISTER It is certified that error appears in the above—identified patent and that said Letters Patent is hereby corrected as shown below:

Column 1, line 65: Before "membrane" please insert -- stress applied to the --.

Column 6, line 12: "socket 33a" should read -- socket 33 --.

"plug 33" should read -- plug 33a --.

Signed and Sealed this

Seventeenth Day of August 1982

[SEAL]

Attest:

GERALD J. MOSSINGHOFF

*Attesting Officer*     *Commissioner of Patents and Trademarks*